(12) United States Patent
Ono

(10) Patent No.: US 6,331,528 B1
(45) Date of Patent: Dec. 18, 2001

(54) METHOD FOR TREATMENT IN GENE THERAPY AND USE OF GUANINE DERIVATIVE THEREFOR

(75) Inventor: Nobukazu Ono, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/557,327

(22) Filed: Apr. 25, 2000

(51) Int. Cl.[7] .......................... A61K 31/70; C12N 15/00; A01N 63/00
(52) U.S. Cl. .................. 514/44; 435/320.1; 424/93.6; 514/45
(58) Field of Search ...................... 514/44, 1, 50

(56) References Cited

U.S. PATENT DOCUMENTS 5,631,236 * 5/1997 Woo et al. .............................. 514/44

OTHER PUBLICATIONS

Georges et. al. Canine T cells transduced with a herpes simplex virus thymidine kinase gene: a model to study effects on engraftment and control of graft–versus–host disease; Transplantation; 66(4) 540–4.*

Guzman, In vivo suppression of injury–induced vascular smooth muscle cell accumulation using adenovirus–mediated transfer of the herpes simplex virus thymidine kinase gene, 1994, Proc. Natl. Acad. Sci. Vol. 91:10732–10736.*

Sekeyama et al. Journal of Med Chem 41:1284–1298 Apr. 1998.*

Ono et al., Antimicrobial Agents and Chemotherapy 42(8):2095–2102 Aug 1998.*

Iwayama et al. Antiviral Research 42:139–148 Jun. 1999.*

* cited by examiner

Primary Examiner—Deborah Crouch
Assistant Examiner—Joseph Woitach
(74) Attorney, Agent, or Firm—Oblon, Spivak, McClelland, Maier & Neustadt, P.C.

(57) ABSTRACT

The present invention relates to a method for inhibiting cell growth whereby a thymidine kinase gene is introduced and expressed in a cell followed by administering a (−)-9-[1,S, 2'R-bis(hydroxymethyl)cyclopropan-1'-yl]methylguanine in an amount sufficient to inhibit cell growth.

10 Claims, 1 Drawing Sheet

METHOD FOR TREATMENT IN GENE THERAPY AND USE OF GUANINE DERIVATIVE THEREFOR

BACKGROUND OF THE INVENTION

1. Field of the Invention

The present invention relates to a method for treatment in gene therapy and use of the specified guanine derivative as the pharmaceutical agent for gene therapy of tumor, restenosis after PTCA and graft vs. host diseases; more specifically, the present invention relates to a method for treatment in gene therapy, comprising the step of administering (administrating) as the pharmaceutical agent for gene therapy, (−)-9-[1'S,2'R-bis(hydroxymethyl)cyclopropan-1'-yl]methylguanine or a derivative convertible to the guanine derivative in animal bodies, into a living subject such as humans; still more specifically, the present invention relates to an use of the guanine derivative as the pharmaceutical agent for gene therapy, wherein the guanine derivative as the pharmaceutical agent is used in combination with the gene used for the gene therapy, which is preferably the gene of an enzyme phosphorylating the guanine derivative, more preferably thymidine kinase gene, particularly the thymidine kinase gene of a virus (for example, herpesvirus).

2. Description of the Related Art

Clinical modalities of the gene therapy of cancer include the following:

1. a modality directly targeting cancer-related genes, comprising introducing cancer suppresser genes such as P53 gene and antisense genes of cancer genes into cancer cells;
2. a modality enhancing immunity against cancer, comprising introducing various cytokine genes and syngenic MHC genes into tumor-infiltrating lymphocytes and cancer cells;
3. a modality introducing suicide genes into cancer cells to permit the cancer cells to be sensitive to drugs, comprising introducing the herpesvirus-thymidine kinase gene (HSV-TK gene) into cancer cells and administering ganciclovir (GCV) as a therapeutic agent of herpesvirus, to kill the cancer cells; and
4. a modality comprising introducing a multi-resistant gene into hematopoietic cells to enhance the resistance against anti-cancer agents and subsequently subjecting the cancer cells to chemical therapies at large doses (see MATSUSHITA Eiki et al., Liver, Gall Bladder and Spleen 34(4): 433–438, 1997).

Clinical protocols using such modalities have been approved for various subjects of cancers, such as melanoma, cerebral tumor, breast cancer, large intestine cancer including colon cancer, lung cancer, ovarian cancer, and kidney cancer. A clinical protocol using the modality described above in 3 has been reported for hepatocellular carcinoma (see Huber, BE, Richards CA, Krenisky TA: Retroviral mediated gene therapy for the treatment of hepatocellular carcinoma: An innovative approach for cancer therapy. Proc. Natl. Acad. Sci. USA 88: 8039–8043, 1991). Recently, a clinical report about cerebral tumor has been issued (see Ram Z. et al., Nat. Med. 3(12), p.1354–1361, 1997).

SUMMARY OF THE INVENTION

1. Problem that the Invention is to Solve

Various methods have been proposed for gene therapies comprising introducing genes into human bodies, but none of the methods is a satisfactory method. Therefore, research works have been promoted about various methods, particularly about pharmaceutical agents therefor, genes therefor and vectors carrying the genes. However, research works about pharmaceutical agents for use in combination with the genes for gene therapies have not made any progress yet. For example, ganciclovir is reported (see S T Clair M H, Lambe C U, Furman P A: Inhibition by ganciclovir of cell growth and DNA synthesis of cells biochemically transformed with herpesvirus genetic information. Antimicro. Agents Chemother. 31: 844–849, 1987). Ganciclovir induces the occurrence of bone marrow suppression and reproductive toxicity, which is a factor regulating the administration of ganciclovir. Aciclovir (ACV) of the same nucleoside-type antiviral agent as ganciclovir has been known, but has an extremely poor therapeutic effect.

In such circumstances, the development of a pharmaceutical agent used for gene therapy, having a particularly high safety profile and an excellent therapeutic effect, is desired as an anti-cancer agent.

It is a purpose of the present invention to develop an excellent pharmaceutical agent which can be used for gene therapy, particularly a pharmaceutical agent with highly efficacious effects in human bodies, in particular, from both the respects of pharmaceutical efficacy and safety profile.

2. Means for Solving the Problem

The present inventors have made investigations so as to solve the problem. Consequently, the present inventors have found that by using the compound represented by the following structural formula (1), (−)-9-[1'S,2'R-bis(hydroxymethyl)cyclopropan-1'-yl]methylguanine or a derivative convertible to the compound in animal bodies (sometimes totally abbreviated as "guanine derivative") as a component of the pharmaceutical agent for gene therapy in combination, preferably with the gene of an enzyme phosphorylating the guanine derivative, particularly with the thymidine kinase gene of a virus, such as herpesvirus, more particularly with the thymidine kinase gene of HSV-1, HSV-2 or VZV as the gene for use, the guanine derivative is phosphorylated, particularly triphosphorylatecl in bodies of animals, such as humans, particularly in cells at a diseased lesion such as tumor cell, to terminate polymerization of DNA chain of which the inhibition is intended and thereby exert cellular toxicity; that the inhibitory action thereof can be exerted on bystander cells; and that the guanine derivative can be used as the pharmaceutical agent for gene therapies of tumor, restenosis after PTCA and graft vs. host diseases. Based on the findings, the present invention has been achieved.

(1)

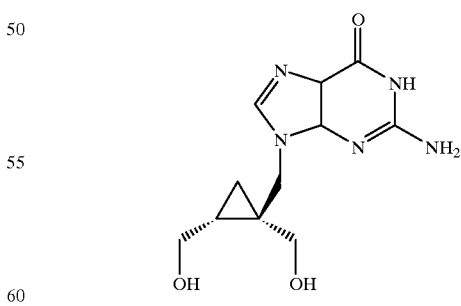

More specifically, the present invention relates to a method for treatment in gene therapy, which comprises administering (administrating) as the pharmaceutical agent for gene therapy (−)-9-[1'S,2'R-bis(hydroxymethyl) cyclopropan-1'-yl]methylguanine or a derivative convertible to the compound in animal bodies (guanine derivative), into a living subject such as humans, which can be used particularly for the therapeutic treatment of tumor, restenosis after PTCA, graft vs. host diseases and the like. Additionally, the method and the pharmaceutical agent for gene therapy used in the present invention encompasses the following inventions.

1. The method described above wherein the gene therapy is for the therapeutic treatment with suicide gene therapy.

The aforementioned gene therapy is the treatment with the pharmaceutical agent for suicide gene therapy.

2. The method described above wherein the treatment is for the therapeutic treatment of humans afflicted with any of tumor, restenosis and graft vs. host diseases.

The treatment is for humans, and therefore the pharmaceutical agent is a therapeutic agent for humans, preferably for treating tumor, restenosis after PTCA, graft vs. host diseases and the like (the term "therapeutic treatment" includes the use of the guanine derivative for therapeutic treatment, amelioration, prevention of exacerbation, prophylaxis, etc.).

3. The method as describe above wherein the pharmaceutical agent of the guanine derivative is for parenteral dosing, particularly intravenous dosing at 0.001 to 10,000 mg/kg per day to humans or for oral dosing at 0.005 to 50,000 mg/kg per day to humans which may be administered thereinto.

4. The method described above wherein the pharmaceutical agent (the guanine derivative) for gene therapy is used in combination with the gene of an enzyme phosphorylating the guanine derivative described above, preferably thymidine kinase gene, more preferably viral thymidine kinase gene.

5. The method described above wherein the gene of an enzyme phosphorylating the guanine derivative is the thymidine kinase gene of herpesvirus (including HSV-1, HSV-2 and VZV).

6. The method described above wherein the thymidine kinase gene is a gene carried on a viral vector to be inserted in a target cell.

As the gene of the enzyme described above, preferably, the viral thymidine kinase gene such as herpesvirus, etc. is employed. The gene can be carried to a target cell requiring the gene by using an appropriate vector (for example, viral vector), or the gene can directly be inserted in cells requiring the gene in bodies, by using for example liposome.

7. The method described above wherein the guanine derivative for the effective component in the pharmaceutical agent is the compound represented by the structural formula (1), and at least one hydroxyl group of the hydroxymethyl group thereof is esterified with amino acid.

EMBODIMENTS OF THE INVENTION

The pharmaceutical agent for gene therapy in accordance with the present invention will now be described hereinbelow in embodiments.

The pharmaceutical agent of the guanine derivative for gene therapy in accordance with the present invention is a pharmaceutical agent for use in gene therapy and can be used for conventionally known methods and gene therapies possibly developed in future, for the treatment, amelioration and prophylaxis of various diseases. The inventive pharmaceutical agent used in the present invention as the effective component comprises the guanine derivative (−)-9-[1'S,2'R-bis(hydroxymethyl)cyclopropan-1'-yl]methylguanine or a derivative convertible to the compound in animal bodies. The pharmaceutical agent for gene therapy is used in combination, preferably with the gene of an enzyme phosphorylating the compound, more preferably with thymidine kinase gene, particularly preferably with the thymidine kinase gene of a virus (herpesvirus described above).

Among various gene therapies, the inventive pharmaceutical agent for gene therapy can be used for a method comprising introducing preferably a suicide gene into a target cell such as tumor cell and thereby suppressing the target cell. The guanine derivatives for use in accordance with the present invention is then used as a prodrug, preferably, which is converted to the triphosphate form as the drug in the target cell through the action of the enzyme gene. In this case, the suicide gene and the prodrug are to be selected. As the suicide gene, preferably, herpes simplex thymidine kinase gene is used. As to the technique, some report tells an example of the use of ganciclovir (see Ram Z. et al., supra.). Hence, the pharmaceutical agent for gene therapy in accordance with the present invention can be prepared and used according to the reported method.

The inventive method for gene therapy can be used widely diseases and the like (including the use for treatment, amelioration, prevention, prophylaxis, etc.). The method is applicable to any of diseases to which genes are applicable. The method is preferably applicable to various diseases such as tumors, restenosis after PTCA, and graft vs. host diseases. The tumors include benign and malignant tumors, cancers developing in various sites and the like. As to the graft vs. host diseases, the organ transplantation includes any organ and any cell type, with no limitation.

The guanine derivative as the effective component of the pharmaceutical agent for use in accordance with the present invention can be used at its free form represented by the structural formula (1), but can be used in any of pharmaceutically acceptable salts, esters and other related derivatives and additionally in derivative forms convertible to the compound represented by the structural formula (1) in patient bodies and animal bodies, for example a derivative of the compound represented by the structural formula (1), wherein both or one of the hydroxyl groups of the hydroxymethyl group is esterified with amino acid, or an isomer derivative (with purine ring) thereof, wherein the carbonyl group present in the guanine ring is in resonance with the hydroxyl group and the hydroxyl group is substituted with (replaced with) hydrogen atom (see Japanese Patent Kokai Publications Nos. JP-A-5-78357, JP-A-6-227982 and JP-A-7-188231, of which the descriptions are incorporated herein by reference.). All these forms are also encompassed within the guanine derivative for use as the effective component of the pharmaceutical agent used in the inventive method.

The pharmaceutical agent used in the inventive method can be dosed orally or parenterally to humans. For the preparation of such dosage form, a necessary oral or parenteral dosage form can be prepared, by utilizing various known formulation techniques.

The dose thereof is appropriately selected, depending on the diseased conditions, severity and systemic conditions of a patient. For parenteral dosing, particularly intravenous dosing, the close is preferably about 0.001 to 10,000 mg/kg per day, more preferably about 0.01 to 1,000 mg/ kg per day and still more preferably about 0.1 to 20 mg/kg per day. For oral dosing, similarly, the close is preferably about 0.005 to 50,000 mg/kg per day, more preferably about 0.05 to 5,000 mg/kg per day and still more preferably about 0.1 to 2,000 mg/kg per day.

The pharmaceutical agent used in the inventive method can be given once or in a divided fashion daily, but is generally given once to three times daily, satisfactorily. Depending on the diseased conditions and the like, the inventive pharmaceutical agent can be administered intermittently or in a concentrated manner.

For the administration of the pharmaceutical agent, preferably, the thymidine kinase gene of virus is required to be introduced. Particularly when a virus vector-generating cell is to be transplanted locally, the pharmaceutical agent is preferably administered after the transplantation of the virus vector-generating cell, so as to sufficiently deliver the virus vector to a lesion.

For the introduction of the thymidine kinase gene, viral integration methods conventionally known or possibly developed in future can be used.

For tumor (see International Patent Kohyou Publication No. JP-A-9-504518), restenosis after PTCA (see International Patent Kohyou Publication No. JP-A-9-504558) and HSV-1 thymidine kinase gene insertion, a method for allowing systemic or local infection with a virus vector is a candidate. As the method, a method for directly injecting locally a solution of the virus vector to be used, a method for directly transplanting a virus vector-generating cell in tumor, and a method for enveloping a virus vector in hydrogel for local retention thereby enhancing the local infectious potency of the virus vector, are presented. As to the application to the cases with graft vs. host diseases, furthermore, a method for integrating a gene ex vivo in a graft resected from a donor and transplanting the graft to a patient is also available (see International Patent Publication WO 97/45142, of which the descriptions are incorporated herein by reference.).

Other than such virus vector, additionally, a method for directly injecting a gene in cells, particularly cellular nuclei and a method for locally delivering HSV-1 thymidine kinase gene by various known physical formulation technology using erythrocyte ghost, liposome, polycation, immunogen (antibody conjugated with an objective gene) and the like can also be used.

Regarding those described above, various reports have been issued. Recently published patent information (see International Patent Publication WO 93/10218, WO 96/05321, WO 97/45142 and WO 97/44065. All the descriptions therein are incorporated in the specification of this application by reference.) can be referenced. Additionally, the gene therapy using ganciclovir (see Ram Z. et al., Therapy of malignant brain tumors by intratumoral implantation of retroviral vector-producing cells, Nature Medicine, Vol. 3, No. 12, 1354–1361, 1997, of which the descriptions are incorporated herein by reference.) can particularly be referenced alike. In this case, the reference is useful, when the pharmaceutical component (guanine derivative) for use in accordance with the invention is used in place of the guanine derivative as the pharmaceutical component ganciclovir.

The pharmaceutical agent used in the inventive method for gene therapy preferably exerts effects in the treatment combination with cytokines such as various interleukins along with the thymidine kinase gene, the pharmaceutical agent can be carried on vectors. The description in the International Patent Kohyou Publication JP-A-9-504518 described above is to be referenced for determining the method therefor. The descriptions are helpful particularly for the method of using vector. When no cytokine is used in accordance with the present invention, the description can be referenced for the use of vector, excluding the description relating to the combined use with cytokines. The description regarding the use of ganciclovir as an interactive drug is referenced for the use of the guanine derivative in accordance with the present invention. Accordingly, the description regarding the use of vector for thymidine kinase gene, which is useful as a reference in accordance with the present invention, is encompassed incorporated within the present specification by reference and composes partially the specification of this application.

The pharmaceutical agent used in the present invention for gene therapy can be used singly in a practical sense, but can also be used in combination with other pharmaceutical agents, therapies and treatments against tumor cells.

In addition to the use of the pharmaceutical agent used in the present invention for gene therapy, also the use of anti-tumor agents, the use of restenosis suppressive agents or the use of the drugs for regulating graft vs. host diseases, each comprising the guanine derivative (-)-9-[1'S,2'R-bis (hydroxymethyl)cyclopropan-1'-yl]methylguanine or a derivative convertible to the compound in animal bodies is contained in the present invention. In this case, the method for gene therapy is just described as one simple example of the invention of the use of the guanine derivative-containing anti-tumor agents, the use of the anti-arteriosclerotic agents or the use of the anti-allergy agents in the treatment.

As to the description of the guanine derivative as the pharmaceutical agents used in the inventive method excluding the pharmaceutical agent for gene therapy, namely the detailed description of the invention relating to the anti-tumor agents, restenosis suppressive agents or drugs for regulating graft vs. host diseases, the guanine derivative to be used as the pharmaceutical component, the dosage recipe, the dosage form, the dose per day, the use for anti-tumor applications, restenosis suppression or regulation of graft vs. host diseases are as described in the description of the pharmaceutical agent for gene therapy. In other words, the description of the guanine derivative as the pharmaceutical agent for gene therapy, excluding the description of the gene for use and the method for using the gene (including the use of vector gene), is also applicable to the description of the invention, unless particularly not required or not contradictory.

Now this application is based on the Japanese Patent Application Ser. No. 629/1999, filed on Jan. 5, 1999, and so the descriptions contained in the Japanese Patent Application Ser. No. 629/1999 is incorporated in the specification of this application by reference.

EXAMPLES

The present invention will be described in detail in the following examples and comparative examples.

Example 1
Cellular Toxicity in HSV-1 Thymidine Kinase Gene-introduced Cell

The cellular toxicities of the quanine derivative for use in accordance with the invention (the compound in the free form represented by the structural formula 1), ganciclovir and aciclovir (Comparative Example 1 and 1') against HSV-1 thymidine kinase gene-introduced cells were tested.

Human lung small cell carcinoma-derived RERF-LC-MA cell was infected with a viral vector prepared by inserting the thymidine kinase gene in a vector derived from Molony mouse leukemia virus. The resulting RERF-LC-MA/LTRNL cell was used. Furthermore, RERF-LC-MA/LZRNL cell with no insertion of any HSV-1 thymidine kinase gene was used as a control cell. The method for preparing these cells and the assay of the cellular toxicities were according to the method reported by Hasegawa et al. [see Hasegawa Y. et al., Am. J. Respir. Cell Mol. Biol. 8 (6) (1993) p. 655–661]. Based on the assay method of cellular toxicity, the cellular toxicities were confirmed by a calorimetric assay method using MTT [3-(4,5-dimethylthiazol-2-yl)-2,5-diphenyl-tetrazolium bromide].

The RERF-LC-MA/LTPNL cell suspension was diluted with a culture medium (E-MEM, 10% FBS) and inoculated at $2\times10^3$ cells/well in a 96-well plate. Then, the pharmaceutical component (guanine derivative) for use in accordance with the invention, ganciclovir and aciclovir were added at various concentrations to these wells. Subsequently, the cellular toxicities were assayed and confirmed by a calorimetric assay humid atmosphere for 4 days and using MTT on day 4.

Figure 1:
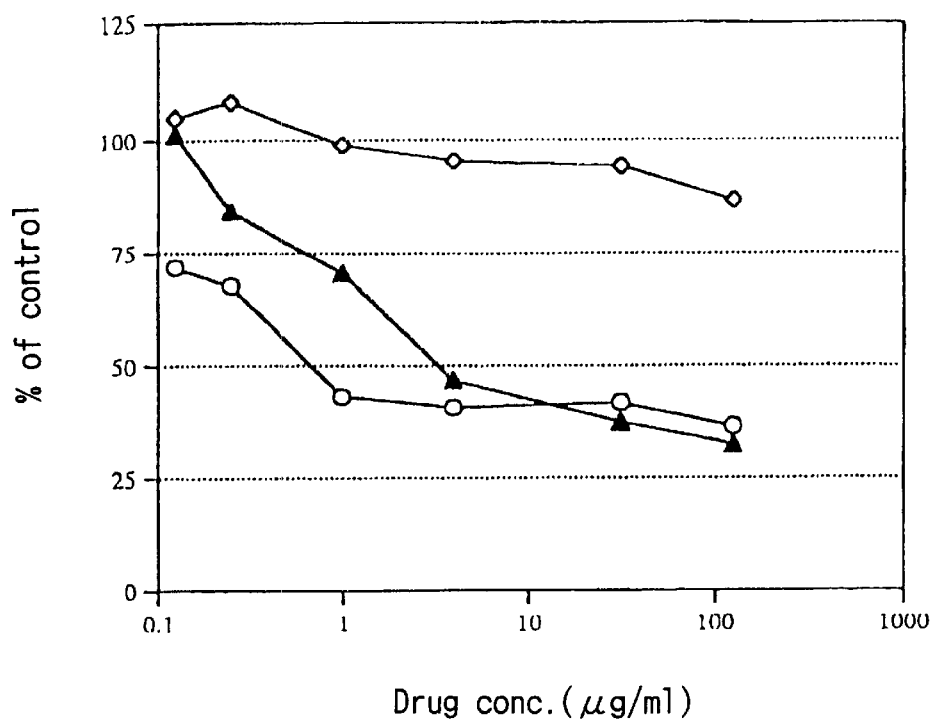
FIG. 1 shows graphs of cellular toxicities in the HSV-1 thymidine kinase gene-introduced cell, as tested in Example 1, wherein—open circle—: invention;
—open diamond—: aciclovir; and
—closed triangle—: ganciclovir.

The IC50 values of the guanine derivative for use in accordance with the invention, ganciclovir and aciclovir, in the RERF-LC-MA/LTRNL cell in which the HSV-1 thymidine kinase gene was expressed, were 0.66 μg/ml or more, 3.2 μg/ml or more and 125 μg/ml or more, respectively (See FIG. 1). On contrast, the IC50 values of the guanine derivative for use in accordance with the invention, ganciclovir and aciclovir in the control RERF-LC-MA/LZRNL cell were 135 μg/ml or more, 201 μg/ml or more and 250 μg/ml or more, respectively. The results indicate that the guanine derivative for use in accordance with the invention exerts more excellent cellular toxicity effect, compared with the conventional products.

Example 2
Effect on the Inhibition of the Growth of Mouse Granulocyte Macrophage Precursor Cell (CFU-GM)

The effects of the guanine derivative for use in accordance with the invention (the free form of the compound represented by the structural formula 1), ganciclovir and aciclovir (Comparative Examples 2 and 2') on the inhibition of the growth of mouse granulocyte macrophage precursor cell (CFU-GM) were tested.

The mouse granulocyte macrophage precursor cell of Okano et al. [see Okano A. et al., Transplantation 48 (1989) p. 495–498].

The effects on the inhibition of the growth of CFU-GM were assayed as follows. From the femur bone marrow of mouse C57BL/6N Crj females of age 10 weeks was prepared bone marrow cell, which was then inoculated at a concentration of $4\times10^4$ cells/ml in a semi-solid culture medium with addition of various concentrations of the guanine derivative, ganciclovir and aciclovir (Iscove's modified Dulbecco's medium, 0.8% carboxymethyl cellulose, 20% FBS, 200 units/ml mouse interleukin-3). The cell was cultured in 37° C. in 5% $CO_2$ in a wet atmosphere on a 35-mm plate for 7 days. The emerging CFU-GM colonies were counted with a differential microscope.

Figure 2:
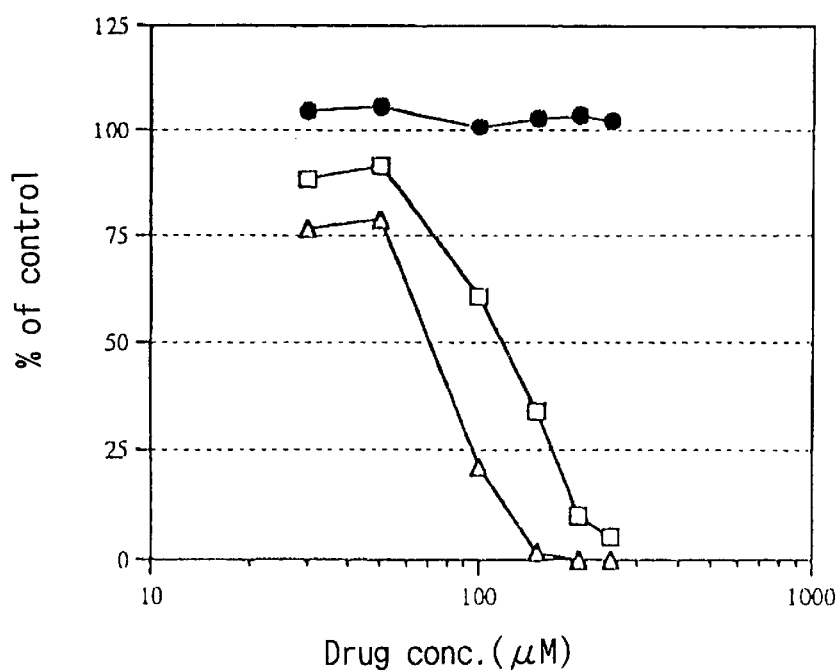
FIG. 2 shows graphs of effects on the inhibition of the growth of mouse granulocyte macrophage precursor cell (CFU-CM) as tested in Example 2, wherein—closed circle—: invention;
—open square—: aciclovir;
—open triangle—: ganciclovir.

The IC50 values of tho guanine derivative for use in accordance with the invention, ganciclovir and aciclovir in the mouse granulocyte macrophage precursor cell (CFU-GM) formed colonies were 66 μg/ml or more, 18 μg/ml and 26 μg/ml, respectively (see FIG. 2).

The results indicate that the bone marrow toxicity of the inventive guanine derivative administered is possibly weaker than those of ganciclovir and aciclovir, which suggests that the inventive guanine derivative is extremely safe.

As apparently shown in the Examples and Comparative Examples, particularly in FIGS. 1 and 2, the pharmaceutical agent used in the present invention, namely the pharmaceutical agent comprising the guanine derivative described above, is extremely useful, compared with conventionally known ganciclovir and aciclovir, in light of both the therapeutic effect and the safety profile.

Advantages of the Invention

The guanine derivative of (−)-9-[1'S,2'R-bis (hydroxymethyl)cyclopropan-1'-yl]methylguanine (including its salts and its derivatives convertible to the compound in animal bodies) as the pharmaceutical agent for gene therapy, is more excellent in terms of both the pharmaceutical efficacy and safety profile as an anti-tumor agent, compared with conventionally known ganciclovir and aciclovir when used. The guanine derivative as the pharmaceutical agent is promising for wide use in the therapeutic treatment, amelioration, exacerbation prevention and prophylaxis of various tumors at various sites and additionally restenosis after PTCA and graft vs. host diseases, particularly in humans.

Still further, the guanine derivative can be used generally widely as the pharmaceutical agent for gene therapy and can additionally be used as an effective component widely and individually for the therapeutic treatment, amelioration and exacerbation prevention and prophylaxis, particularly of tumors, restenosis after PTCA and graft vs. host diseases.

What is claimed is:

1. A method of inhibiting cell growth comprising
   introducing and expressing an isolated thymidine kinase gene in a cell; and
   administering a (−)-9-[1'S,2'R-bis(hydroxymethyl) cyclopropan-1'-yl]methylguanine, a pharmaceutically acceptable salt thereof or ester thereof in an amount sufficient to inhibit cell growth.

2. The method of claim 1, wherein said thymidine kinase gene is a Herpes Simplex virus thymidine kinase gene or a Varicella Zoster virus thymidine kinase gene.

3. The method of claim 1, wherein said cell is in a human patient.

4. The method of claim 3, wherein said inhibiting cell growth comprises inhibiting tumor growth in said human patient.

5. The method of claim 3, wherein said inhibiting cell growth comprises treating restenosis after PTCA.

6. The method of claim 3, wherein said effective amount comprises 0.001 to 10,000 mg/kg per day.

7. The method of claim 6, wherein said effective amount comprises 0.01 to 1,000 mg/kg per day.

8. The method of claim 3, wherein said inhibiting cell growth comprises treating graft vs. host disease.

9. The method of claim 1, wherein said introducing comprises introducing a virus vector comprising the thymidine kinase gene.

10. The method of claim 1, wherein said introducing comprises introducing a liposome comprising the thymidine kinase gene.

* * * * *